Jan. 7, 1964 W. FLEMER III Plant Pat. 2,339
MAPLE TREE
Filed Jan. 25, 1963
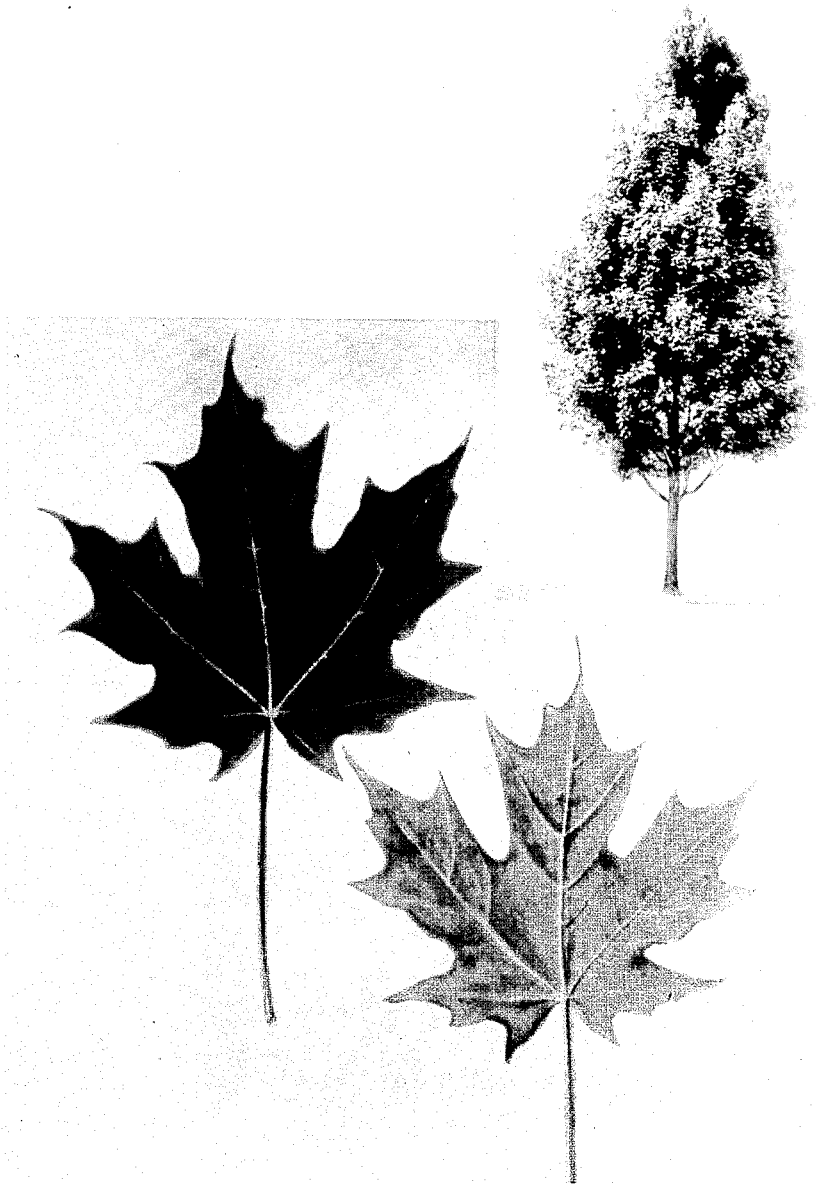
Inventor.
William Flemer III
By: Robb & Robb
Attorneys.

United States Patent Office

Plant Pat. 2,339
Patented Jan. 7, 1964

2,339
MAPLE TREE

William Flemer III, Princeton, N.J., assignor to Princeton Nurserymen's Research Associates, Princeton, N.J., a partnership Filed Jan. 25, 1963, Ser. No. 254,033
1 Claim. (Cl. Plt.—51)

The present invention relates to a new and distinct variety of maple tree which was originated by me by crossing an unnamed and unpatented variety botanically known as *"Acer saccharum"* identified as "P.N. #15" with another unnamed and unpatented variety of *"Acer saccharum"* identified as "P.U. #3."

In selecting this new variety from numerous seedlings derived from the aforementioned breeding, as grown under my direction and supervision in the nursery of my assignee in Plainsboro township, Plainsboro, New Jersey, my choice was made by virtue of the fact that the new variety bore exceptionally handsome dark green foliage in a year when the foliage of other sibling seedlings in the same block were severely browned by leaf scorch during a hot and dry period of summer weather. My choice was also influenced by the fact that this selected seedling was about one-fourth (¼) larger than the average size of the other seedlings in the same block. Continued tests and observations of the new seedling, and all progeny thereof derived from budding in the nursery aforementioned, convinced me that it was definitely distinguished from the parent varieties, as well as from all other varieties of which I am aware, as evidenced by the following unique combination of characteristics which are outstanding therein:

(1) A rapid habit of growth;

(2) A straight central trunk which branches excurrently into a narrow ovate head;

(3) Thickened strong crotches where the branches join the main trunk;

(4) Attractive and distinctive dark green foliage, with the dark green color being consistently maintained in years when other sugar maple trees in the same area have turned brown during summer periods of heat; and (5) Good insect resistance, particularly to the feeding activities of leaf hoppers, with consequent high resistance of the young shoots to terminal injury and stunting, as compared with other varieties grown under the same conditions in the same area.

The accompanying drawing shows a typical specimen tree of the new maple variety as depicted in black and white to illustrate its general form and habit of growth, and also typical leaf specimens on an enlarged scale as depicted in color, and illustrating the upper and under surfaces of the leaves.

The following is a detailed description of my new variety, with color terminology in accordance with Munsell Color Chart, except where general color terms of ordinary dictionary significance are obvious:

Parentage: Seedling.

*Male parent.*—An unnamed seedling of *"Acer saccharum"* identified as "P.N. No. 15."

*Female parent.*—An unnamed variety of *"Acer saccharum"* identified as "P.U. No. 3."

Propagation: Holds its distinguishing characteristics through succeeding propagations by budding (sometimes called bud-grafting).

Locality where grown and observed: Plainsboro township, Plainsboro, New Jersey.

Tree: Medium size; vigorous; very upright; medium tall; dense, narrow-ovate head of branches; unusually rapid growing as a young tree, hardy.

*Trunk.*—Stocky; thick in relation to crown of tree; smooth when young.

*Branches.*—Stout; short; smooth-barked; dense excurrent pattern of branching, forming a narrow, upright crown; branches form strong, enlarged crotches where they rise from the central leader.

*Lenticels.*—Scattered; large.

Foliage:

*Leaves.*—Exceptionally thick; leathery; large; very long (from 14 to 16 cm. along midrib); wide (from 16 to 20 cm.); 5 major lobes plus 8 minor lobes, with major lobes having very long, tapering points averaging about 2 cm. in length. Upper surface—smooth. Under surface—smooth, with occasional short hairs and tufts of hairs in axils of veins. Margin—undulate. Color (in summer)—upper surface: Dark Green, Plate 7.5GY3/4; under surface: Pale Glaucous Green, Plate 7.5GY6/4. Petiole—from 12 to 14 cm. long; slender; color: Flushed Red on upper surface.

Flowers: None observed; flowers usually not significant in the species.

Fruit: None observed; fruits usually not significant in the species.

Weather Resistance: Foliage is entirely free of physiological leaf scorch when other varieties grown under the same conditions in the same New Jersey area are severely scorched during exceptionally hot and dry summer weather.

Insect resistance: Young shoots are highly resistant to terminal injury and stunting due to feeding activities of leaf hoppers, as determined by comparison with other varieties grown under the same conditions in the same New Jersey area.

I claim:

A new and distinct variety of maple tree, substantially as herein shown and described, characterized particularly as to novelty by the unique combination of a rapid habit of growth in the young tree stage, straight central trunk branching excurrently into a narrow-ovate head, strong, thickened crotches where the branches join the main trunk, attractive and distinctive dark green foliage which consistently maintains its dark green color when other sugar maple trees grown under the same conditions in the same area turn brown during exceptionally hot and dry periods of summer weather, and good insect resistance.

No references cited.